United States Patent [19]

Knight

[11] Plant 4,046

[45] May 3, 1977

[54] ROSE PLANT NAMED PARFAIT

[75] Inventor: Clysten Knight, Richmond, Ind.

[73] Assignee: DeVor Nurseries, Inc., Pleasanton, Calif.

[21] Appl. No.: 671,667

[22] Filed: Mar. 29, 1976

[51] Int. Cl.[2] ..... A01H 5/00
[52] U.S. Cl. ..... Plt./22
[58] Field of Search ..... Plt./22

*Primary Examiner*—Robert E. Bagwill
*Attorney, Agent, or Firm*—Rummler & Snow

[57] ABSTRACT

A new variety of rose plant of the floribunda type particularly intended for greenhouse culture and the production of cut flowers, this plant being distinguished by the pleasing and unusual color contrast in its blooms which show a heavy suffusion of red extending in progressing stages from the periphery of the petals toward the base of the petals as the blossom opens passing through a cream colored central portion to a light yellow area at the base of the petals. The new plant is further distinguished by its uniform production of fine quality, medium sized blooms throughout the entire year, under greenhouse conditions, and by lasting quality of the blooms which are carried by sturdy stems and peduncles.

3 Drawing Figures

BACKGROUND OF THE NEW PLANT

This new rose plant originated as a sport of "Minuette" (U.S. Plant Pat. No. 3,162) and was found by me on May 5, 1970, among plants of the parent variety growing under glass at Richmond, Ind., and was selected for propagation and test because of its very extraordinary coloration as compared with its parent. Propagation of this sport was first done by budding, at my direction, at Livermore, Calif., and successive generations of this new variety propagated under glass, by budding, have demonstrated the new plant to have other advantages over its parent variety, in addition to color, all of which appear to be firmly fixed and to hold true from generation to generation.

Asexual propagation of this new rose variety has been and is now being done at Pleasanton, Calif., and at Hamilton City, Calif.

DESCRIPTION OF THE DRAWING

My new variety of rose plant is illustrated by the accompanying photographic drawings which, in full color, show in FIG. 1, four stages of the bloom from a tight bud with sepals just cracked to a full opened flower; in FIG. 2, parts of the plant to show top and bottom sides of typical foliage, the form of the sepals, and uncracked bud, young wood and two pieces of mature wood to illustrate its unusual coloring; and in FIG. 3, a full face view of a mature flower. The colors shown are as nearly true as can be reasonably expected to be reproduced by conventional photographic procedures.

DESCRIPTION OF THE NEW PLANT

The following is a description, in detail, of my new variety of rose plant with color designations according to the R.H.S. Colour Chart published by The Royal Horticultural Society at London, England, in collaboration with the British Colour Council, the following data being from observations of greenhouse plants made at Livermore, Calif., and San Leandro, Calif.

THE PLANT

Origin: Seedling.
Parentage: Minuette (U.S. Plant Pat. No. 3,162).
Classification: Botanic — Floribunda. Commercial — Greehouse rose.

Form: Bush.
Height: 4 to 6 feet, when established.
Growth: Sturdy and very vigorous.
Habit: Compact and moderately upright, free branching with strong canes and stems.
Foliage: Quantity — Abundant.
*Leaves.*—Number — eight to 10 on flower stem spaced 1½ to 2½ inches apart.
*Size.*—Large — About 4¼ inches wide and 6½ inches long.
*Shape.*—Odd pinnate.
Leaflets: Number — three to seven.
*Size.*—About 1⅞ inches wide and 3¼ inches long.
*Shape.*—Ovate, with entire margin uniformly serrate.
*Color.*—Upper side — Green 137A. Under side — Greyed Green 191B.
*Texture.*—Leathery.
*Aspect.*—Glossy .
*Ribs and Veins.*—Prominent on both sides.
*Petioles.*—1 to 1½ inches long. Petioles have small thorns, 1/16 to 3/16 inches long and spaced about ½ inch apart, on under side and spines and prickles on top side.
*Petiolule.*—1/16 inch long.
Rachis: Have adnate stipules and erect, pointed auricles. Both stipules and auricles have hairs tipped with glands around their edges.
Main Stems: Color — On side facing sunlight — Greyed Orange 175A. All shaded portions — Green 138B.
*Thorns.*—Size — ⅛ to ½ inch long from a base ⅛ to ⅝ inch long and 1/32 to 5/32 inch wide.
*Color.*—Greyed-Orange 165B.

THE BUD

Before bud breaks:
*Size.*—Small.
*Form.*—short pointed ovoid with a conspicuous neck and with foliaceous appendages on the surface of the bud some of which extend beyond the tip of the bud for a distance of about ⅓ the length of the bud.
*Opening.*—Bud opens slowly.

When sepals first divide:

*Size.*—Length — 1¼ to 1⅜ inches. Width — ½ inch at base, ¾ inch at center.

*Form.*—Pointed ovoid.

*Color of Petals.*—Red-Purple 57C at margins blended to Yellow 4A at base of petal.

As petals unfurl to quarter-open bud:

*Size.*—Diameter 1½ to 1¾ inches at center, 1 to 1⅛ inches across base.

*Color.*—Red Purple 57B at margins blending into Yellow 4A at base of petals.

Sepals: Permanent. The sepals are hooded over the bud until the bud cracks and then the sepals recede progressively outward until the bloom is fully opened when the sepals flatten and remain standing at right angles to the calyx.

*Color.*—Inside — Green 138B. Outside — Green 138B blending to Greyed-Orange 165B near center on side facing sunlight.

*Shape.*—Spear-shaped, some with fine white hairs. Some sepals have two appendages near the sepal tip. These do not have white hairs at the margins but rather they have hairs tipped with purple glands spaced about 1/32 inch apart around the margins. Those sepals without appendages have uniform white hairs around the entire margin and no glands.

Calyx:

*Shape.*—Pear-shaped.

*Size.*—Large, ⅝ to ¾ inch wide and 1¼ to 1⅜ inch long.

*Aspect.*—Smooth.

*Splitting.*—Calyx does not split.

Peduncle:

*Length.*—2 to 2½ inches.

*Strength.*—Erect and very sturdy.

*Color.*—Greyed-Orange 175A on side facing sunlight. Green 138B on shaded side.

*Hairs.*—None.

*Prickles.*—Many small prickles except for about ¼ to ½ inch from top.

THE FLOWER

Blooming Habit: Profusely and continuously the year around under glass, blooming freely in fall and winter.

Size: Medium, 3 to 3½ inches in diameter and 1¼ to 1½ inches in depth when fully opened.

Borne: Singly and also in clusters of two to four flowers on strong, sturdy stems.

Shape: High center when bloom first opens becoming globular as bloom matures.

Petalage: Double. Petal count is inconsistent, majority averaging in the range of 37 to 48 petals, with some blooms having only 30 to 35 petals.

*Arrangement.*—Imbricated with petaloids forming a small ball hiding pistils and stamens.

*Shape.*—Basically round — some petals being notched and some are pointed at the tip.

*Aspect.*—Moderately velvety.

*Texture.*—Slightly more firm than soft.

*Color.*—Outer petals: Inside — Mainly Red 47A shading to Yellow 3B at the base. Reverse — Margin:Red 47A; Center: Red 56B; Base: Yellow 10B. Inner petals: Inside — Mainly Red Purple 47D, shading to Yellow 3A at the base. Reverse — Margin: Red Purple 47D; Center: Red 36C; Base: Yellow 3B speckled with Red 57B. The margin color of the reverse side of the petals widens and blends toward the base as the flower opens. The insides of the petals, when the bloom is about one-quarter open, have a suffusion of the red color over about 60% of the petal area and when the flower is fully opened, this red color covers about 85% of the petal surface.

Petaloids: 17 to 20 in number.

*Size.*—3/16 to ⅝ inch wide and ⅜ to ¾ inch long.

*Color.*—Margin — Red 53D. Base — Yellow 3B.

Persistence: Drops cleanly after full bloom.

Disease Resistance: This flower resists mildew and rust, as observed at Hamilton City, Calif.

Fragrance: Slight — very mild cinnamon.

Lasting Quality: On plant — 18 to 22 days. As cut flower — 7 to 9 days.

REPRODUCTIVE ORGANS

Stamens:

*Anthers.*—185 to 195 in number.

*Arrangement.*—Introrse.

*Color.*—Yellow Orange 14A.

Filaments: Length —1/16 to 3/16 inch.

*Color.*—Near anther — Red Purple 57B. At base — Yellow 9C.

*Pollen.*—Color — Yellow 14A.

Pistils: Number — 152 to 167.

*Styles.*—1/16 to 3/16 inch long and unattached to each other.

*Stigmas.*—Color — Yellow 5C.

Ovaries: Covered with fine stiff white hairs.

FRUIT

The fruit is fertile and round in shape. Its color at maturity is Orange-Red 30C.

The main advantages of my new variety of rose plant reside in its consistent and fine production of fine quality blooms throughout the entire year as a greenhouse plant, the sturdy stem and peduncle and the lasting quality of the flowers, and the distinctive coloration of the flowers during their several stages from bud to full bloom.

In many respects, this new rose plant is similar to its parent "Minuette" (U.S. Plant Pat. No. 3,162), the particular difference being in the color of the blooms. The basic color of "Minuette" is ivory with a very distinct and uniform red margin around the entire periphery of each petal, except at the base. My new variety has no distinct red margin on its petals but rather has a very heavy suffusion of red which spreads progressively from a wide petal margin toward the base, as the bloom opens, to the extent that when the bloom is fully opened, the suffusion of red on the inside of the petals covers about 85% of the petal surface. When the flower is about half open, the outside of the petal has three distinct colors, namely red, ivory and yellow, while the inside of the petal has only the two distinct colors of red and yellow.

My new variety has exactly the same distinctive bark color response to sunlight and shading as its parent, a factor which further distinguishes the new plant from other roses.

I claim:

1. A new and distinct variety of rose plant substantially as herein shown and described, characterized by the distinctive red, ivory and yellow coloration of its blooms in which a basic suffusion of red spreads progressively from the petal margin to near the base as the bloom develops from bud opening to full maturity.

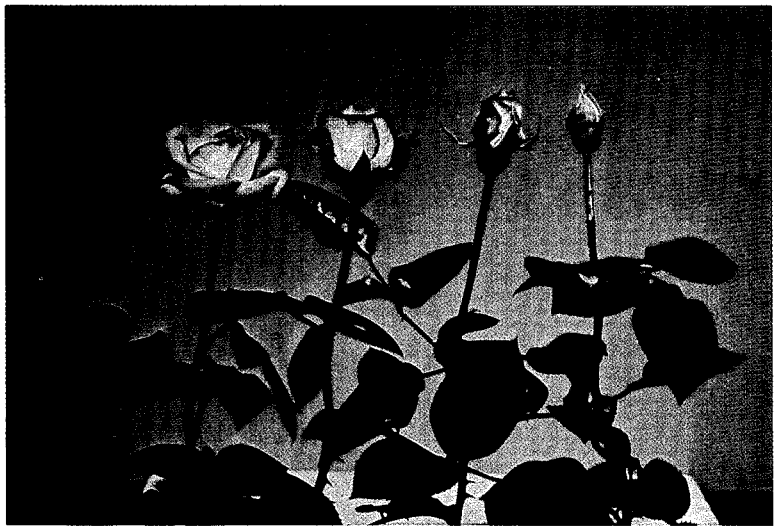
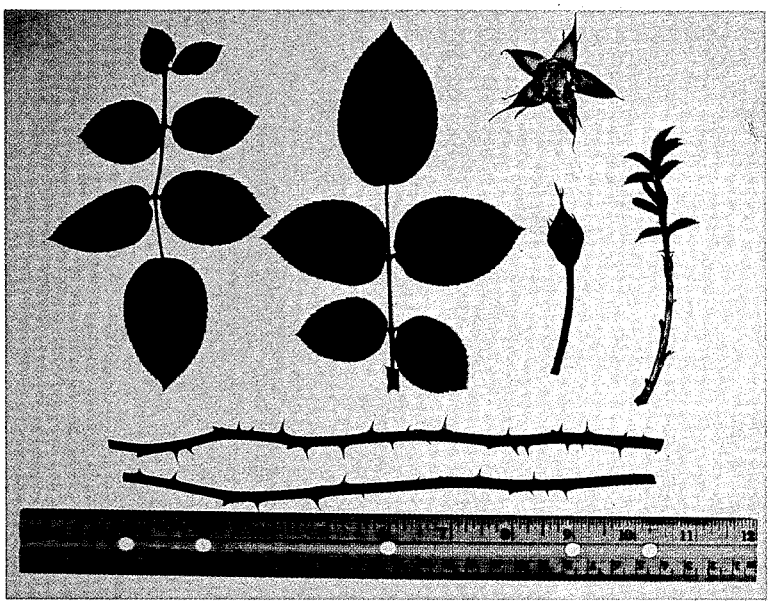

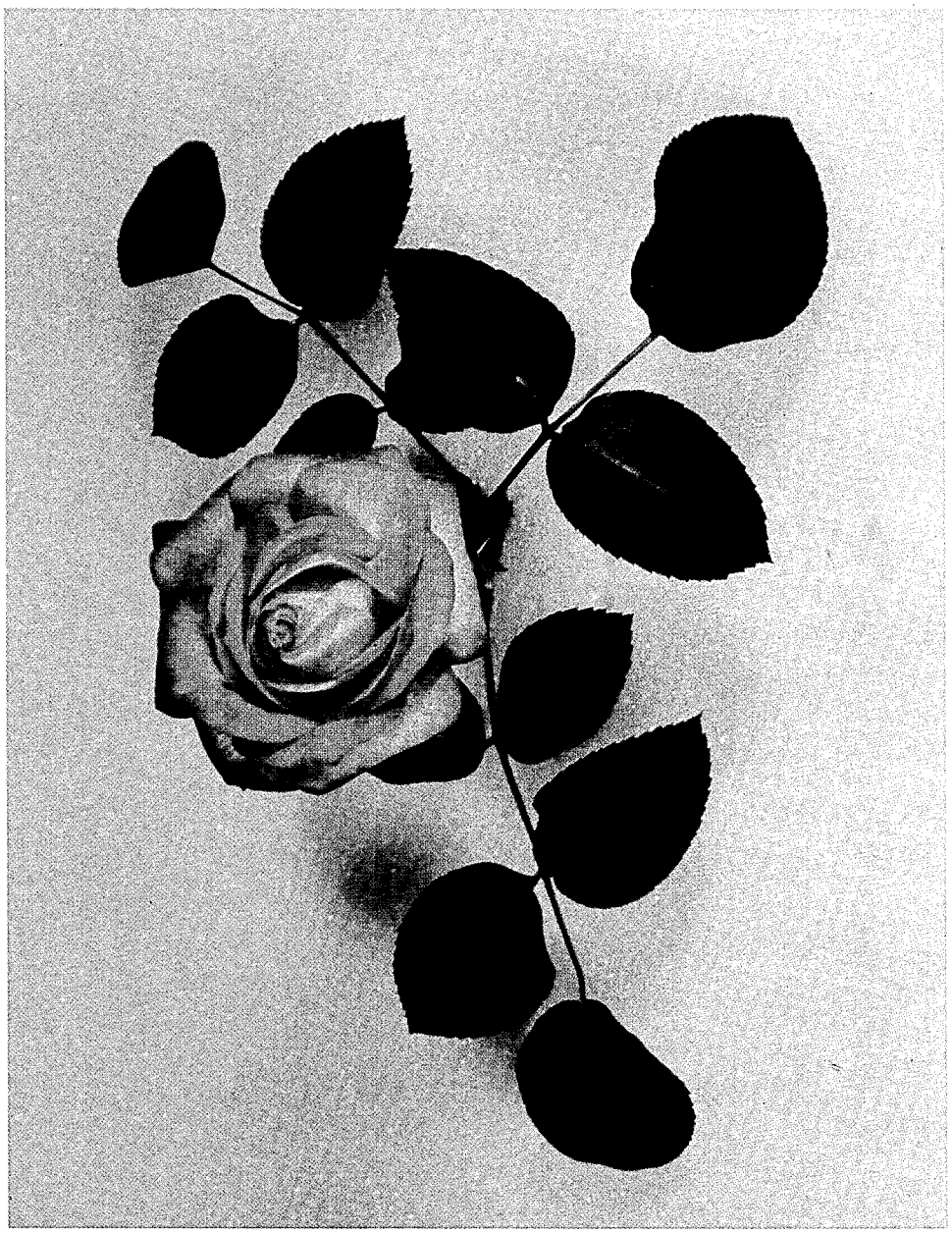

* * * * *